United States Patent
Le Couëdic et al.

(10) Patent No.: US 10,420,590 B2
(45) Date of Patent: Sep. 24, 2019

(54) VERTEBRAL FIXATION DEVICE

(71) Applicant: IMPLANET, Martillac (FR)

(72) Inventors: Régis Le Couëdic, Bordeaux (FR); Denis Pasquet, Aix-en-Provence (FR)

(73) Assignee: IMPLANET, Martillac (FR)

( * ) Notice: Subject to any disclaimer, the term of this patent is extended or adjusted under 35 U.S.C. 154(b) by 0 days.

(21) Appl. No.: 15/565,733

(22) PCT Filed: Apr. 7, 2016

(86) PCT No.: PCT/FR2016/050799
§ 371 (c)(1),
(2) Date: Oct. 11, 2017

(87) PCT Pub. No.: WO2016/166448
PCT Pub. Date: Oct. 20, 2016

(65) Prior Publication Data
US 2018/0078286 A1    Mar. 22, 2018

(30) Foreign Application Priority Data

Apr. 17, 2015 (FR) .................................. 15 53424

(51) Int. Cl.
*A61B 17/70* (2006.01)
(52) U.S. Cl.
CPC ...... *A61B 17/7043* (2013.01); *A61B 17/7049* (2013.01); *A61B 17/7053* (2013.01); *A61B 17/7067* (2013.01)
(58) Field of Classification Search
CPC .......................................... A61B 17/70–7046
See application file for complete search history.

(56) References Cited

U.S. PATENT DOCUMENTS

| | | | | |
|---|---|---|---|---|
| 9,247,964 | B1* | 2/2016 | Shoshtaev | A61B 17/70 |
| 9,675,386 | B2* | 6/2017 | Akbarnia | A61B 17/8869 |
| 2006/0235393 | A1* | 10/2006 | Bono | A61B 17/7032 606/278 |
| 2008/0208256 | A1* | 8/2008 | Thramann | A61B 17/70 606/246 |
| 2009/0131982 | A1* | 5/2009 | Schwab | A61B 17/7001 606/246 |

(Continued)

FOREIGN PATENT DOCUMENTS

EP    0928603 A1    7/1999

OTHER PUBLICATIONS

Written Opinion of the International Searching Authority dated Jun. 23, 2016, issued in corresponding International Application No. PCT/FR2016/050799, filed Apr. 7, 2016, 6 pages.

(Continued)

*Primary Examiner* — Nicholas J Plionis
*Assistant Examiner* — Steven J Cotroneo
(74) *Attorney, Agent, or Firm* — Christensen O'Connor Johnson Kindness PLLC

(57) ABSTRACT

A vertebral fixation system comprising two fixation parts which each have a pedicular element that can be engaged in a vertebral pedicle and are connected to each other by a connecting element. The connecting element is a flexible strip, the pedicular elements are screws, and each fixation part comprises a fixation head on a rod secured to means for adjustably locking the flexible strip under tension in relation to the head.

13 Claims, 3 Drawing Sheets

(56) References Cited

U.S. PATENT DOCUMENTS

| | | | |
|---|---|---|---|
| 2010/0106195 A1* | 4/2010 | Serhan | A61B 17/0642 |
| | | | 606/279 |
| 2012/0221056 A1 | 8/2012 | Hutton | |
| 2012/0259369 A1 | 10/2012 | Hammer | |
| 2013/0072983 A1* | 3/2013 | Lindquist | A61B 17/7049 |
| | | | 606/278 |
| 2014/0094851 A1* | 4/2014 | Gordon | A61B 17/7001 |
| | | | 606/264 |
| 2014/0277149 A1* | 9/2014 | Rooney | A61B 17/7053 |
| | | | 606/263 |
| 2018/0042647 A1* | 2/2018 | Cowan | A61B 17/7043 |
| 2018/0228516 A1* | 8/2018 | Armstrong | A61B 17/7035 |
| 2018/0228518 A1* | 8/2018 | Carruth | A61B 17/7049 |

OTHER PUBLICATIONS

International Preliminary Report of Patentability dated Oct. 17, 2017, issued in corresponding International Application No. PCT/FR2016/050799, filed Apr. 7, 2016, 1 page.

International Search Report dated Jun. 23, 2016, issued in corresponding International Application No. PCT/FR2016/050799, filed Apr. 7, 2016, 3 pages.

Written Opinion of the International Searching Authority dated Jun. 23, 2016, issued in corresponding International Application No. PCT/FR2016/050799, filed Apr. 7, 2016, 7 pages.

\* cited by examiner

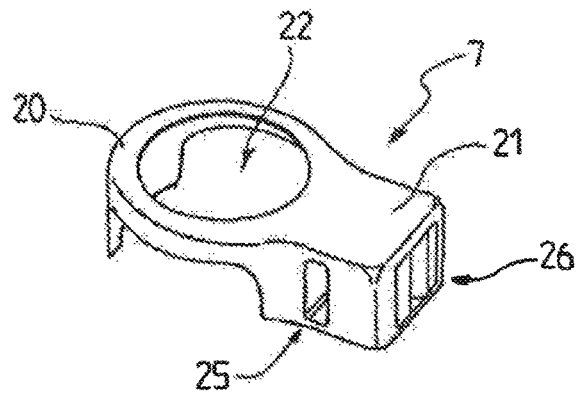
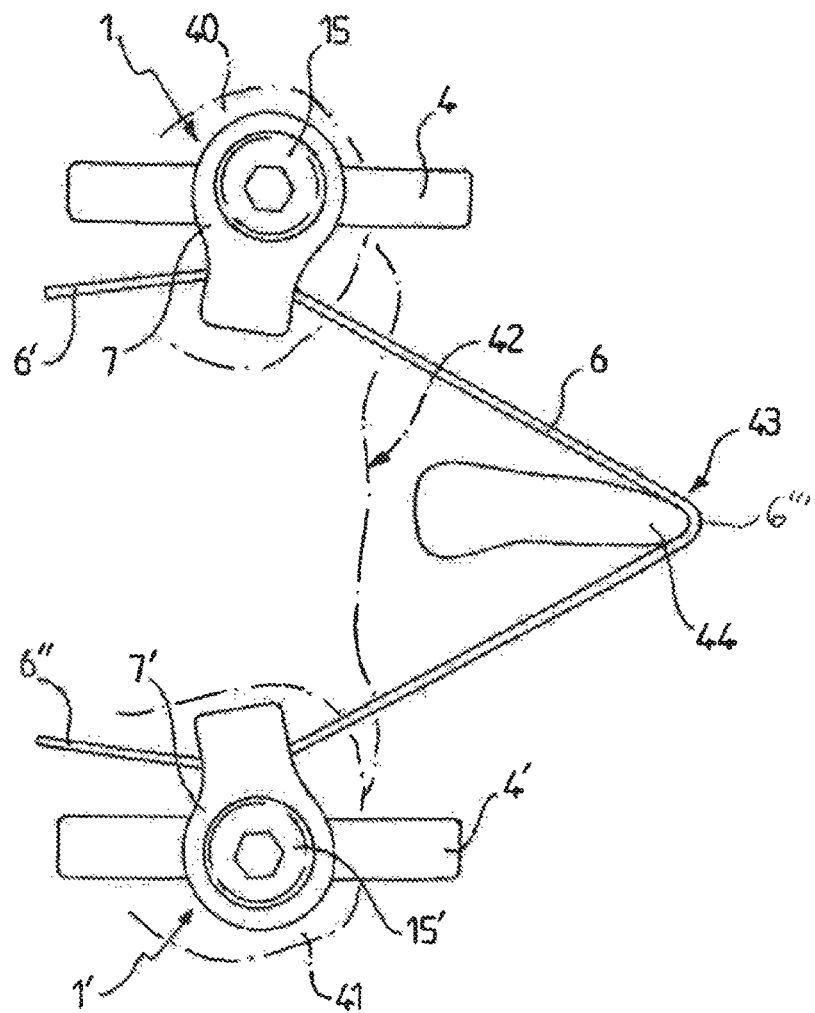
FIG. 2
FIG. 3

VERTEBRAL FIXATION DEVICE

FIELD OF THE DISCLOSURE

Embodiments of the present disclosure relate to a vertebral anchoring system comprising two anchoring components which each have a pedicle element for engagement in a vertebral pedicle and are connected to each other by a linking element.

It also relates to the anchoring components themselves, and to a vertebral anchoring method for rigidly connecting two adjacent vertebrae to each other.

It has a particularly important but not exclusive application in the consolidation of the vertebral column in cases of damage and, more particularly, when one of the vertebrae is of poor quality, for example on account of osteoporosis or an accident.

BACKGROUND

It is known that the intervertebral discs may be subject to compression, herniation, or arthritic intervertebral degeneration.

To manage the patients, there are techniques that require a surgical intervention.

A first technique involves replacement of the damaged disc with an intervertebral disc prosthesis. Such a replacement procedure is difficult for the surgeon to perform and poses a risk of loosening under the effect of the considerable shearing forces that arise in particular when the prosthesis is in the position of maximum flexion.

A second technique involves performing intervertebral arthrodesis, an operation by which the two vertebrae adjacent to the damaged disc can be fused. This blocks the degeneration of the disc, on account of the suppression of any mobility between the two vertebrae concerned.

It is an improvement of this technique that forms the subject matter of the present disclosure.

It is known that such a technique involves the use of a device for stabilizing the two vertebrae, which device comprises screws that are intended to be screwed into the vertebrae and are rigidly connected to each other by a rigid linking element. It is thereby possible to avoid excessive mechanical stresses being applied to the intervertebral disc.

This technique has its disadvantages, however, requiring in particular the introduction of screws into the vertebrae, which procedure is sometimes impossible if the vertebrae are in a poor state and/or are not wide enough in the area of the fixation.

Anchoring devices are known (FR 2 913 330) which are formed by the assembly of two anchoring components which each have a pedicular nail and are connected to each other by a rigid link.

However, although such a system ensures good stability in the degraded bone, it has the disadvantage of being complicated to assemble, and the pedicular nails may moreover be at inclinations that are incompatible on account of the configuration of the vertebra.

SUMMARY

The present disclosure aims to overcome these disadvantages or others and to make available a vertebral anchoring system, component and method that are improved over the prior art in terms of meeting the requirements that arise in practice, especially in that it permits greater flexibility, in that it avoids any element intruding into a weakened vertebral bone if a solid vertebra is present adjacent to the damaged vertebra, and in that it has good stability, all this at a low cost and/or at a lower cost than with the devices of the prior art.

It also has the advantage of simple handling, allowing it to be easily fitted in place by the surgeon.

To this end, the disclosure proposes in particular a vertebral anchoring system comprising two anchoring components which each have a pedicle element for engagement in a vertebral pedicle and are connected to each other by a linking element, characterized in that the linking element is a flexible band, in that the pedicle elements are screws, in that each anchoring component has a head for fixing to a rod which is rigidly connected to means for adjustably blocking the flexible band under tension with respect to the head, and in that it has two rods corresponding to the fixing heads.

The idea of the system is to control the movements of the degraded vertebra with respect to the more solid adjacent vertebra by a link to the spinous process of the vertebra above or below (to its apophysis) by tensioning both sides of the band.

Here, the wedging of the braid or band by the blocking means will be able to permit its longitudinal path by reproducing what the ligaments of the vertebral column do naturally.

It will thus be possible for the range of the movements to be limited without being completely blocked, which partially avoids all the stresses being transferred to the free disc situated adjacent to the vertebrae that are blocked in movement relative to each other, which otherwise generates the well-known phenomenon of the "hinge" effect, this time risking damaging the adjacent disc that is still in good condition.

The disclosure will moreover create a return force applied to the screws, which force returns them to their seat and thereby avoids the disadvantages of the consolidating cements that are generally used with the screws of the prior art. Such cements pose problems of temperature (necessary for the good polymerization of the cement) and moreover make it impossible to re-adjust the screw once it has been blocked in the compound.

In advantageous embodiments, use is moreover and/or furthermore made of one or more of the following provisions:

- The fixing head of the anchoring component is rigidly connected to a ring which is provided with the blocking means;
- The fixing head comprises a body which is in the shape of a cup, traversed laterally by the rod perpendicularly with respect to the pedicle screw, and is provided with an internal thread in its upper part, for fixing the rod by way of a compression screw, and the ring comprises a first through-orifice which can be clipped by deformation onto the upper periphery of the fixing head, a second lateral through-orifice for passage of the band, and a third orifice for insertion of the means for blocking the band in the ring;
- The fixing head comprises an upper part which is cylindrical or shaped as a portion of a cylinder with a first diameter, the first orifice being cylindrical with a diameter matching the first diameter, with which it is designed to cooperate by friction before the compression screw is screwed in, and with which it is designed to be blocked during the clamping of the screw.

This blocking arises from the widening or spacing apart of the walls of the internal thread of the upper part of the head, on account of the compression that the head of the compression screw itself exerts on its edges.

This has the result of pressing the outer wall of the head onto the inner wall of the first orifice and of blocking as a consequence of lateral compression.

The fixing head comprises an upper part provided with a retaining groove or rib, and the first through-orifice of the ring is provided with a rib or groove of corresponding shape designed to be engaged with force one inside the other;

The blocking means comprise a holding component that is insertable into the third orifice of the ring, the holding component being at least partially in the shape of a squeezable wedge, for blocking the band passing through the second orifice;

The holding component has a cross section in the shape of a tuning fork, of which the prongs comprise external non-return teeth, and of which the handle has a rounded end, and the third orifice has side walls, which are provided with non-return teeth matching those of the holding component, and a bottom with a shape matching that of the end of the handle, for wedging the band between the two;

The pedicle screw has a round or oblong end mounted pivotably in rotation in the lower part of the fixing head, and the head has a joining structure between the cylindrical wall of the rod and the screw end.

The disclosure also relates to an anchoring component as described above. It likewise relates to an anchoring method using a system as described above.

It moreover relates to a vertebral anchoring method for rigidly connecting two adjacent vertebrae to each other, in which method two pedicle screws are screwed into the opposite pedicles of a vertebra, a rod is slid through a fixing head for fixing each screw to the rod, and a compression screw is screwed onto the rod through the upper part of the head, characterized in that, before the compression screw is screwed in, a ring is clipped onto the upper periphery of each head, the ring comprising a first through-orifice that can be clipped by deformation onto the upper periphery, a second lateral through-orifice for passage of a band, and a third orifice for insertion of means for blocking the band on the fixing head, the flexible band is placed on the adjacent vertebra and in the blocking means of each fixing head, the band is blocked on a head, and one starts to tension the flexible band by pulling on the other side, after which one tensions the whole assembly before finally blocking the band with respect to the remaining head.

The movement of the adjacent vertebra with respect to that of the base vertebra is thus secured completely, but gently, by preventing the flexion of one with respect to the other, and this in accordance with the functioning of the vertebral column.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

FIG. 1A is a sectional view along $I_A$-$I_A$ in FIG. 1.
FIG. 1B is a sectional view along $I_B$-$I_B$ in FIG. 1.
FIG. 1C is a partial sectional view, similar to the section along $I_B$-$I_B$, of a variant of the component in FIG. 1.
FIG. 2 is a perspective view of the ring of the component in FIG. 1.
FIG. 3 is a schematic plan view illustrating the anchoring system using two anchoring components according to FIG. 1, two rods, and the flexible band tensioned around the apophysis of a vertebra.

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figure 1:
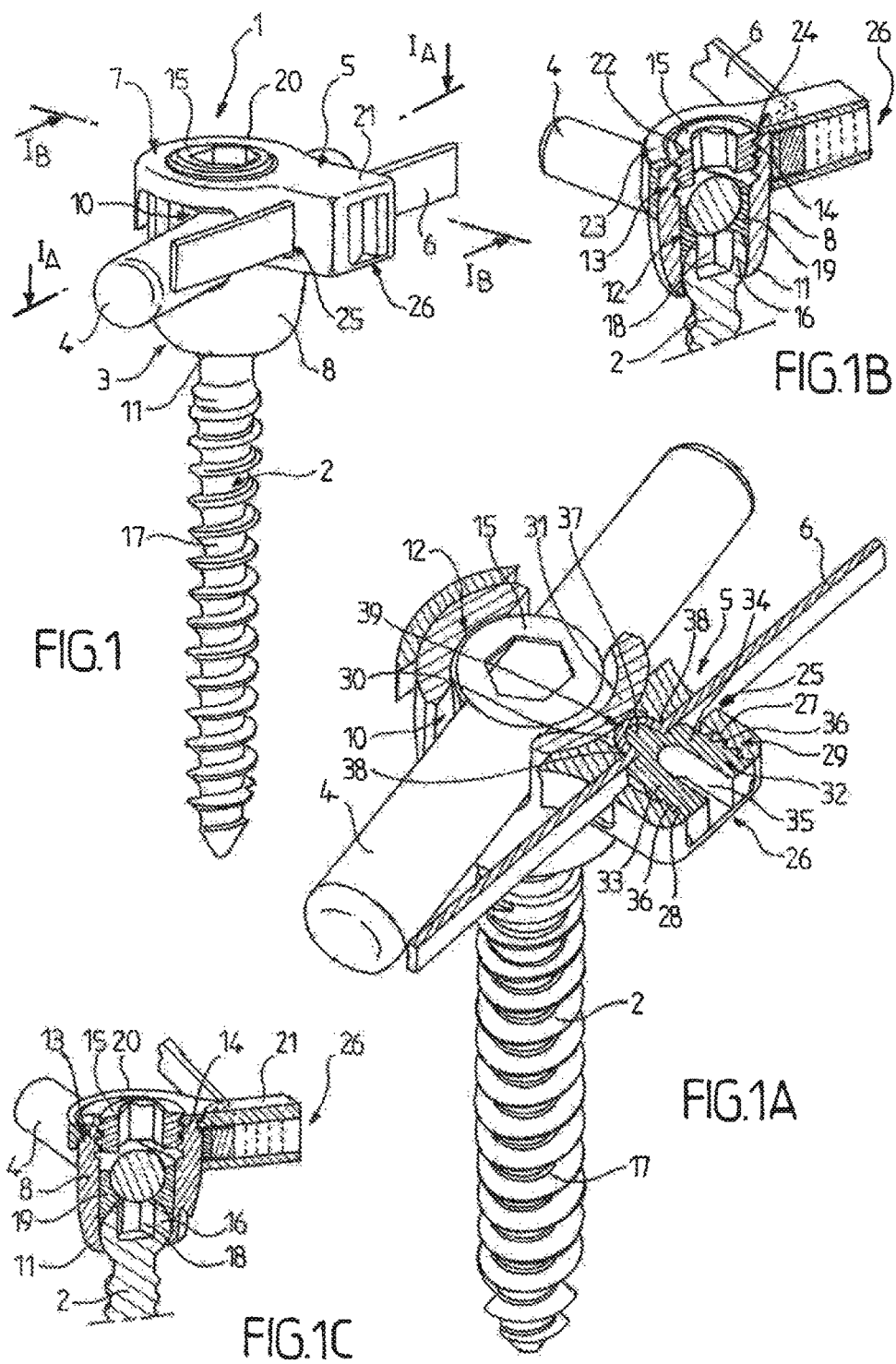
FIG. 1 is a perspective axonometric view of an anchoring component according to a first embodiment of the disclosure.

FIG. 1 shows an anchoring component 1 having a pedicle screw 2 that can be screwed into a vertebral pedicle (not shown).

The component has a head 3 for fixing to a rod 4 which is rigidly connected to means 5 for adjustable blocking of a flexible band 6 under tension.

The band 6 is flat, for example of braided polyester, with a thickness of 1 to 3 mm and a width of 6 mm.

The blocking means 5 comprise a ring 7 rigidly connected to the head 3, which comprises a cup-shaped body 8 recessed all the way through in its lower part or bottom 9 to allow the pedicle screw 2 to pass through, and it has two lateral notches 10, open toward the top, for lateral passage of the rod 4 which is engaged therein.

The body 8, made of titanium for example, is cylindrical and comprises a rounded bottom and a cylindrical internal recess 12 in which the screw is passed and blocked in the axial direction.

Its lower part 13 comprises an internal thread 14 for fixing the rod, which has been introduced into the lateral notches 10, by a compression screw 15, which will thus press the rod onto the head 16 of the pedicle screw 2.

The latter comprises a screw body 17 provided with a screw thread of a type known per se.

The head 16 of the screw (cf. FIG. 1B) is provided with a socket 18 to permit screwing by a tool. It is partially spherical and bears on the bottom 11 of the cup of the body 8 of the fixing head 3 with which it cooperates frictionally in rotation and in longitudinal abutment.

After the screw 2 previously introduced into the anchoring component 1 has been screwed in, and after introduction of the rod 4, the ring 7 is put into place, this being done after a joining/guiding/supporting component 19 has been introduced above the screw head, which component 19 has a semicylindrical shape at one side (rod) and an annular shape at the other side (screw head).

The ring 7 (cf. also FIG. 2) is a component made of titanium for example, its cross section in the shape of a keyhole, with a first cylindrical portion 20, and a second portion 21 which is parallelepipedal, with a width smaller than the diameter, or substantially parallelepipedal.

The first cylindrical (or substantially cylindrical) portion 20 is provided with an internal cylindrical bore 22 or first orifice comprising a narrowed upper part 23 which, with the top 24 of the fixing head, forms a block against axial movement.

The internal bore 22 cooperates frictionally, by cylinder/cylinder contact, with the outer surface of the cylindrical upper part 13 of of the body 8.

Once the ring has been placed with friction onto this upper part, the clamping screw 15 for compression is screwed in.

This screwing-in, for which the head of the screw 15 is designed, provides a slight expansion of the volume that it occupies during the clamping, for example of the order of 0.2 mm, which deforms the bore of the lug by lateral compression, which blocks all movement of the ring with respect to the lug.

FIG. 1C shows another embodiment, in which the first orifice 22 of the ring comprises a rib which is snap-fitted with force into a corresponding channel or groove.

The ring 7 comprises a second orifice 25 for passage of the band 6, namely a lateral through-orifice in the shape of a vertical slot with a width and thickness slightly greater (for example with a play of 1 mm) than those of the band 6, in order to allow the latter to pass through easily.

The ring 7 moreover comprises a third orifice 26 that passes through the portion 21 perpendicularly with respect to the second orifice 25. The portion 21 comprises a first parallelepipedal part 27 (cf. FIG. 1A) comprising non-return teeth 28 on both of its opposite inner side faces 29 (for example three teeth), for example on the side faces situated in planes parallel to the axis of the screw 2 and, on the other side of the through-orifice 25 with respect to this first part 27, a second parallelepipedal part 30 of smaller width, but of the same height as the first orifice part 27, for example opening out on the periphery of the outer face 31 of the upper part of the fixing component 3.

The means 5 for blocking the band 6 moreover comprise a holding component 32 in the shape of a tuning fork, of which the prongs are squeezable and/or insertable by deforming in the third orifice 26.

More precisely, the component 32 comprises a cross section (cf. FIG. 1A) in the shape of a tuning fork with two prongs 33 and 34 which are separated by a recess 35 and which are themselves provided, on their outer faces opposite the inner side faces 29, with non-return teeth 36 matching the teeth 28, with which they will engage with a progressive snap-fit action when the component 32 is inserted with force into the first part 27.

The component 32 moreover comprises a protruding tongue which forms an end handle 37 of the tuning fork and which will be inserted into the second part 30 of the orifice in order to wedge the band 6 between it and the lateral edges 38 and the bottom 39 of the second part when the component 32 is completely engaged in the third orifice 26.

To do this, a slight play will be allowed between the walls of the handle and the wall of the second orifice part, in order to allow the band to be sufficiently squeezed and blocked in position, the calculation of the play being within the scope of a person skilled in the art.

Figure 4:
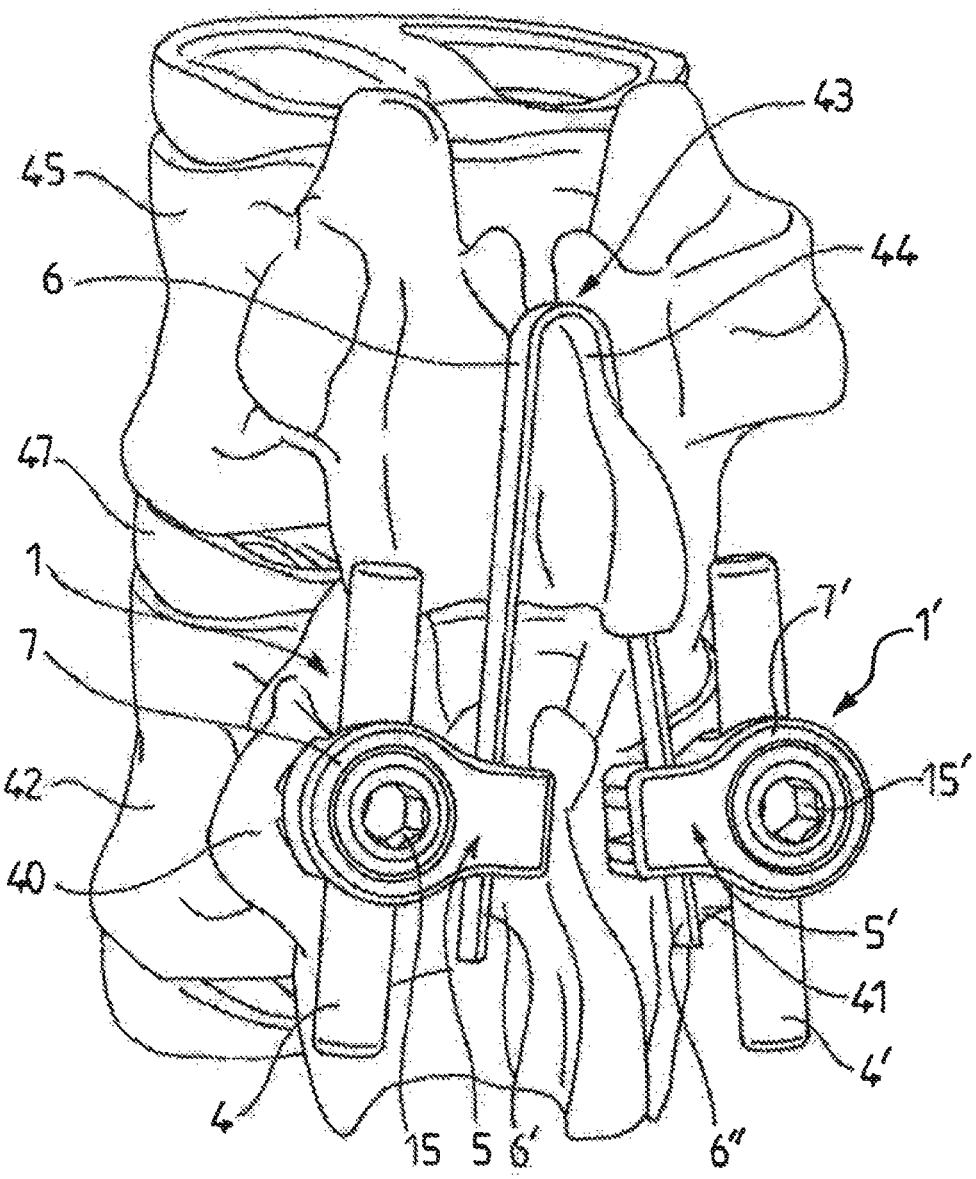
FIG. 4 is a perspective view of a system comprising two anchoring components according to the embodiment of the disclosure more particularly described here, in position on two adjacent vertebrae. It will be noted that only one anchoring pedicle screw has been shown here per rod; each rod will of course be able to comprise several of the screws in order to block the movements of at least two adjacent vertebrae.

FIGS. 3 and 4 illustrate the anchoring system according to the embodiment of the disclosure more particularly described here, using two anchoring components 1, 1' in the two opposite pedicles 40 and 41 of the vertebra 42, each component being provided with screws 2, 2' and being fixed to the rods 4, 4' by way of the compression screws 15, 15'.

The band 6 is blocked on each side by the blocking means 5, 5' and engages at 43 on the epiphysis 44 of the vertebra 45 (cf. FIG. 4).

We will now describe, with reference to FIGS. 1A and 4, the implementation of the anchoring using the system according to the embodiment of the disclosure more particularly described here.

The surgeon wishing to relieve the intervertebral disc 47 between the vertebra 42 (solid) and the vertebra 45 (fragile) begins by fixing the pedicle screws, provided beforehand with their fixing heads, in the pedicles 40 and 41 of the vertebra 42, doing so in a manner known per se, by screwing the screws through the heads, using a screwdriver or tool that drives the socket 18.

He then engages the rods 4, 4' on the heads, then clips the rings 7, 7' onto the upper periphery of each head.

Before or after this, while the rings still retain a certain degree of freedom in rotation with respect to the corresponding fixing head, he slides the respective end portions 6' and 6" of the band 6 into the third orifice.

He then places the central part 6''' of the band on the pineal crest 44 of the adjacent vertebra 45.

Then, on the one hand, he blocks the head 3 on the rod 4 by screwing the compression screw 15 and, on the other hand, he blocks the end portion 6' of the band with the blocking means 8, by inserting the whole of the holding component 32 into the third orifice of the corresponding ring, the teeth 28 of the orifice cooperating by progressive engagement and by deformation then resuming their position in the teeth 36 of the tuning fork, on account of the relative elasticity of the prongs of the tuning fork.

The dimensions of the elements are for their part designed to wedge the band in the recess formed by the second part 30 of the third orifice removably, the calculation of the dimensions being within the scope of a person skilled in the art.

Using a tool of a known type, the surgeon then tensions the band 6 by pulling on the end portion 6" through the as yet unstressed blocking means 8', the fixing head 3' for its part having been blocked on the rod 41 by screwing of the compression screw 15'.

Then, once the required tension on the crest 44 has been obtained (for example by way of a dynamometric tensioner), the end 6" is definitively blocked with respect to the head 3'.

As will be appreciated, and as is also apparent from the above, the present disclosure is not limited to the embodiments more particularly described. Instead, it includes all variants thereof, in particular those in which the blocking means are different, those in which the pedicle screws have double threads, or those in which the snap-fit engagement of the rings on the fixing head is effected by cone/cone contact, for example with an angle of conicity of the Morse taper type and with a deformable blocking tongue in the lower part.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A vertebral anchoring system comprising two anchoring components which each have a pedicle element comprising a pedicle screw for engagement in a vertebral pedicle and are connected to each other by a linking element, wherein the linking element is a flexible band and wherein each anchoring component has a fixing head configured for fixing to a rod which is rigidly connected to a ring into which can be inserted a means for adjustably blocking the flexible band under tension with respect to the fixing head, wherein the ring comprises a first through-orifice configured to be clipped by deformation onto the upper periphery of the fixing head, a second lateral through-orifice configured for passage of the band, and a third orifice configured for insertion of the means for blocking the band into the ring, and wherein said anchoring system includes two rods corresponding to said fixing heads.

2. The system as claimed in claim 1, wherein each fixing head comprises a body which is in the shape of a cup, traversed laterally by the rod perpendicularly with respect to the pedicle screw, each fixing head having an upper part provided with an internal thread, for fixing the rod by way of a compression screw.

3. The system as claimed in claim 2, wherein the upper part of the each fixing head is cylindrical or shaped as a portion of a cylinder with a first diameter, the first orifice is cylindrical with a diameter matching the first diameter, with which it is designed to cooperate by friction before the compression screw is screwed in, and with which it is designed to be blocked during clamping.

4. The system as claimed in claim 2, wherein the upper part of the each fixing head is provided with a retaining groove or rib, and wherein the first through-orifice of the ring is provided with a rib or groove of corresponding shape designed to be engaged with force one inside the other.

5. The system as claimed in claim 1, wherein the blocking means comprise a holding component that is insertable into the third orifice of the ring, the holding component being at least partially in the shape of a squeezable wedge, for blocking the band passing through the second orifice.

6. The system as claimed in claim 5, wherein the holding component has a cross section in the shape of a tuning fork, of which the prongs comprise external non-return teeth, and of which the handle has a rounded end, and wherein the third orifice has side walls, which are provided with non-return teeth matching those of the holding component, and a bottom with a shape matching that of the end of the handle, for wedging the band between the two.

7. The system as claimed in claim 1, wherein the pedicle screw has a round or oblong end mounted pivotably in rotation in a lower part of each fixing head, and wherein each fixing head has a joining structure between the cylindrical wall of the rod and said screw end.

8. The system as claimed in claim 1, wherein said ring is placed onto an upper part of the fixing head.

9. The system as claimed in claim 1, wherein the compression screw is screwed onto the rod.

10. The system as claimed in claim 1, further comprising blocking means that comprise a holding component that is insertable into the third orifice of the ring, the holding component being at least partially in the shape of a squeezable wedge, for blocking the band passing through the second orifice.

11. A vertebral anchoring method for rigidly connecting two adjacent vertebrae to each other, comprising:
   screwing first and second pedicle screws into the opposite pedicles of a vertebra;
   sliding first and second rods through first and second fixing heads associated with the first and second pedicle screws, respectively;
   screwing a compression screw onto each rod through an upper part of each fixing head;
   clipping a ring onto an upper periphery of each fixing head, each ring comprising a first through-orifice that can be clipped by deformation onto said upper periphery, a second lateral through-orifice for passage of a flexible band, and a third orifice for insertion of means for blocking the flexible band on said fixing head;
   placing a flexible band on an adjacent vertebra and in the ring of each fixing head;
   blocking said flexible band on the first fixing head by inserting in said first fixing head a first means for blocking the band;
   tensioning said flexible band by pulling on the other side of the flexible band; and
   blocking the flexible band with respect to the second fixing head by inserting in said second fixing head a second means for blocking the band.

12. A vertebral anchoring system comprising:
   a first rod and a second rod;
   a first anchoring component having a first head configured to be fixed to the first rod, and a first pedicle screw for engagement in a vertebral pedicle;
   a second anchoring component having a second head configured to be fixed to the second rod, and a second pedicle screw for engagement in a vertebral pedicle;
   a flexible band interconnecting the first and second anchoring components;
   first and second rings configured to be rigidly connected to the first and second heads, wherein each first and second ring comprises a first through-orifice configured to be clipped by deformation onto the upper periphery of the head of the respective anchoring component, a second lateral through-orifice configured for passage of the flexible band, and a third orifice configured for insertion of a band retainer that adjustably secures the flexible band under tension to the ring.

13. The system as claimed in claim 12, further comprising first and second band retainers inserted into the third orifices of the first and second rings, respectively, and configured to adjustably secure the flexible band under tension to the respective rings.

* * * * *